US010330529B2

(12) United States Patent
Poret

(10) Patent No.: US 10,330,529 B2
(45) Date of Patent: Jun. 25, 2019

(54) SYSTEM AND METHOD FOR CHARACTERIZATION OF TRACER LIGHT OUTPUT AND VELOCITY

(71) Applicant: The United States of America as Represented by the Secretary of the Army, Washington, DC (US)

(72) Inventor: Jay C. Poret, Sparta, NJ (US)

(73) Assignee: The United States of America as Represented by the Secretary of the Army, Washington, DC (US)

(*) Notice: Subject to any disclaimer, the term of this patent is extended or adjusted under 35 U.S.C. 154(b) by 384 days.

(21) Appl. No.: 15/246,687

(22) Filed: Aug. 25, 2016

(65) Prior Publication Data

US 2017/0261370 A1 Sep. 14, 2017

Related U.S. Application Data

(60) Provisional application No. 62/306,144, filed on Mar. 10, 2016.

(51) Int. Cl.
| | |
|---|---|
| *G01P 3/36* | (2006.01) |
| *G01J 1/42* | (2006.01) |
| *G01N 21/01* | (2006.01) |
| *G01N 21/84* | (2006.01) |
| *F42B 12/38* | (2006.01) |

(52) U.S. Cl.
CPC .......... *G01J 1/4228* (2013.01); *F42B 12/382* (2013.01); *G01N 21/01* (2013.01); *G01N 21/84* (2013.01); *G01P 3/36* (2013.01)

(58) Field of Classification Search
CPC ....... G01J 1/4228; G01N 21/01; G01N 21/84; F42B 12/382; G01P 3/36
USPC .......................................................... 356/28
See application file for complete search history.

(56) References Cited

U.S. PATENT DOCUMENTS

| | | | | |
|---|---|---|---|---|
| 4,845,690 A * | 7/1989 | Oehler | ................... | G04F 10/00 368/113 |
| 5,349,853 A * | 9/1994 | Oehler | ..................... | F41J 5/06 102/425 |
| 7,751,718 B2 * | 7/2010 | Sage | .................. | H04N 7/17309 398/115 |
| 2015/0308802 A1 * | 10/2015 | Chua | .................... | F42B 12/382 102/513 |

OTHER PUBLICATIONS

Reilly, S., The Establishment of Threshold Criteria for Automated Acceptance Test Equipment Based on Battlefield Use of Tracer Ammunition, 26th International Symposium on Ballistics, Sep. 12-16, 2011, Miami, Florida.

* cited by examiner

*Primary Examiner* — Mark Hellner
(74) *Attorney, Agent, or Firm* — Lisa H. Wang

(57) ABSTRACT

System and methods for simultaneous characterization of tracer light output and velocity by arranging a plurality of photodetectors along the flight path of the tracer and transmitting the detected light output over large distances using an array of analog/digital converter units arranged to correspond to each photodetector. The system can be scaled and configured to operate and control the photodetectors from a remote location.

18 Claims, 7 Drawing Sheets

SYSTEM AND METHOD FOR CHARACTERIZATION OF TRACER LIGHT OUTPUT AND VELOCITY

RELATED APPLICATIONS

The present application claims the benefit of U.S. Provisional Application No. 62/306,144, filed Mar. 10, 2016, which is incorporated herein by reference as if set forth in its entirety.

RIGHTS OF THE GOVERNMENT

The inventions described herein may be manufactured and used by or for the United States Government for government purposes without payment of any royalties.

FIELD OF INVENTION

The current invention relates to tracer bullets and specifically to simultaneous measurement of the light output and ballistic velocity of tracer bullets fired from a gun.

BACKGROUND OF THE INVENTION

Tracers are referred to as bullets that emit visible light when they are fired from the barrel of a gun. These specialized bullets are created by pressing pyrotechnic material into the small hollow cavity in the back of a bullet. When the bullet is fired, the pyrotechnic material is ignited which causes the bullet to emit light thereby creating a visible aid for the soldier to aim his weapon. Tracers are critical for insuring that successive bullets strike their intended target.

Modern tracers are produced both in the United States and other countries. Most tracer manufacturing facilities are high rate production facilities producing thousand of tracers per hour. To ensure the tracers meet military specifications, representative tracers are taken from the production lot and fired on a test range. At this facility, tracers are tested at night by firing a specified number of rounds and observers score the tracer light intensity by how well they can see it with their unaided eyes. No optics or instrumentation are used in these measurements.

The observers are typically placed at different locations to score by how "well" the tracer rounds perform during flight. For example, if an observer cannot see the tracer it is determined to be a "blind". If the tracer's light intensity appears to be dim it is determined to be "dim". At specific distances (depending on the round), the tracer should be at full light intensity. The performance specification for specific rounds (e.g. M62) states how many blinds, muzzle flashes, and dims are allowed for a lot to pass the acceptance test.

One of the biggest drawbacks with this kind of testing is the subjective nature of the tracer evaluation. Human observers evaluate the brightness of the tracer with their eyes. It is well established that different people have different levels of visual acuity. This is due to the makeup of the cones and rods that are part of the eye's retina. Over time the rods and cones undergo changes that affects one's ability to discern an object's brightness. When tracers are tested there is NO quantative data generated other than if the tracer is bright, dim, or blind (not lit or emitting no light). So the manufacturer has no way to quantitatively compare a specific lot of tracers against another lot other than using a subjective system of "blind", "dim", or "bright" cateogories. Additionally tracer velocity, another requirement for tracer testing, is measured using a separate system. This adds further time delays and expense to measuring overall tracer performance.

Over the past several years, an alternative system was developed for automating tracer intensity measurements. This system described in "The establishment of threshold criteria for automated acceptance test equipment based on battlefield use of tracer ammunition", by S. Reilly (26th International Symposium on Ballistics Miami, Fla., Sep. 12-16, 2011), uses Ethernet based video cameras placed at each observer station to capture images of the tracer. By comparing both human observations and the pixel values obtained from the images, the researchers attempted to develop pixel threshold values that could be used to automate the detection of bright, dim, and blind tracers. One of the big issues with this approach is the very small optical cross section of the tracer. A light output tracer only occupies a small number of pixels within the imagers field of view (FOV). Additionally, when tracers are tested on a test range, they are fired from a test weapon at a rate of approximately 1 tracer per second. To keep up with the pace of testing, very rapid pass/fail decisions need to be made to keep up with the test flow. Due to the rapid nature of this testing, camera based systems quantifying pixels taken from an image is not an ideal choice for this kind of measurement due to the large amounts of data generated and the time required to process such data.

Thus, a need exists for a reliable system to quickly, consistently and quantitatively test a tracer's light output. Such system may simultaneously provide velocity data having the added benefit of reducing the time required to test tracers, reduce waste, and provide more substantial information on the tested round.

SUMMARY OF THE INVENTION

It is an object of the invention to provide for a system and method that quantitatively characterizes a tracer's light output and velocity.

In one aspect of this invention a system is provided comprising a tracer that emits light, an acoustic trigger, a photosensor system, a light signal transmitter system, and a data collection and processing system.

In another aspect of this invention, the light signal transmitter system comprises at least one coupled A/D transmitter and A/D receiver pair, wherein the pair is connected to a corresponding photodetector unit with a corresponding signal converter. The A/D transmitter and A/D receiver pair is coupled by a single or multimode fiber optic cable.

In another aspect of this invention, the photosensor system comprises a plurality of photodetectors and its corresponding signal converter such as a current preamplifier or resistor. Each photodetector is comprised of a light detector and a lens, and optionally a filter.

In another aspect of this invention, a remote control system may be incorporated into the system to remotely operate the photosensor system. Such remote control system comprises an ethernet switch, a serial terminal server, and at least one RS-232-to-fiber converter pair that is connected to a photosensor system.

It is a further object of the invention to provide for a system to simultaneously provide for a tracer's velocity using the same light characterization output data generated by the photosensor system.

It is a further object of the invention to provide methods to quantitatively and simultaneously characterize a tracer's light output and velocity information by firing a tracer emitting light, collecting such emitted light using a plurality of photodetectors coupled to an A/D receiver and transmitter pair, wherein the transmitters sends the light signal to a data collecting and processing system.

BRIEF DESCRIPTION OF THE DRAWINGS

Further features and advantages of the present invention may be understood from the drawings.

DETAILED DESCRIPTION

Figure 1:
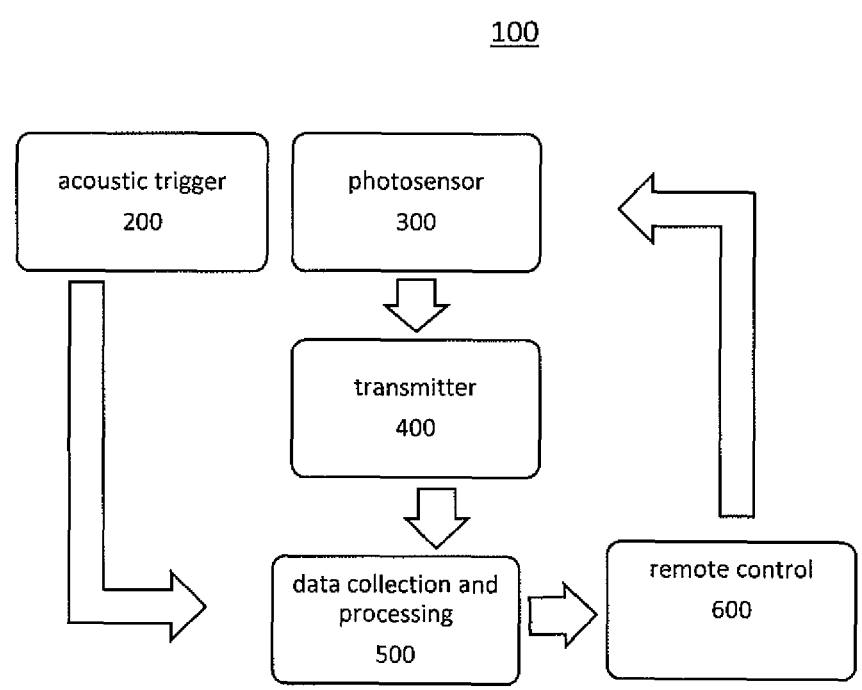
FIG. 1 is a flowchart of the main components of a tracer light characterization system.

Described herein is a tracer characterization system that simultaneously measures a fired tracer's emitted light intensity (e.g. light cause by heat as well as luminescent light) and its average velocity. FIG. 1 is a flowchart illustrating the general units of the tracer characterization system 100, which is composed of an acoustic trigger 200 coupled to the data collection and processing system 500, a photosensor system 300, which receives light signals emitted from the tracer and transmits those light signals to the light signal transmitter system 400. The light signal transmitter system 400 transmits light signals over long distances to the data collection and processing system 500. Optionally, a remote control system 600 may be added to control the photosensor system from a distant location. Each of the subsystems in the tracer characterization system 100 is described in more detail below.

Acoustic Trigger

Figure 3:
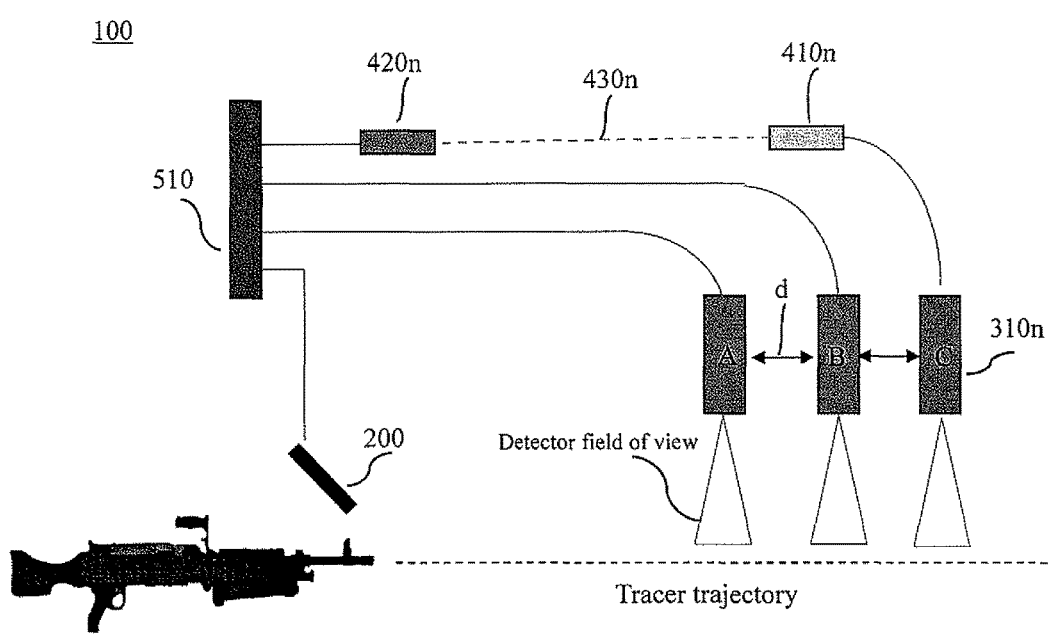
FIG. 3 is a diagram of an exemplary tracer light output characterization system.

The acoustic trigger 200 as illustrated in FIGS. 1 and 3, is composed of an acoustic sensor (available from Kapture Group, sound trigger MD1505) that generates a square wave (TTL pulse) when a gun is fired. The acoustic trigger 200 upon processing the sound from the gun generates an electrical trigger that is coupled to the data collection and processing system 500. The acoustic trigger initiates collection of the data generated by a tracer as it traverses each detector's focal view.

Photosensor System

Figure 2A:
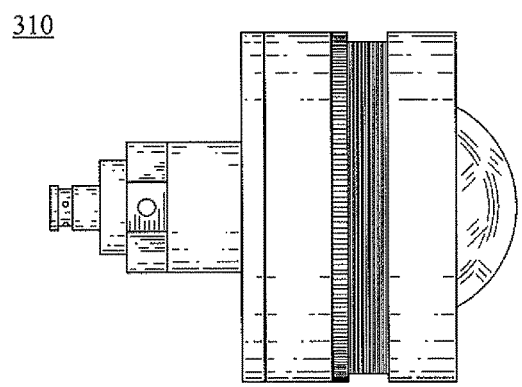
FIG. 2A is an illustration of an exemplary silicon photodetector coupled to a glass aspheric condenser lens.

FIG. 2A illustrates an exemplary photodetector unit 310 in a photosensor system 300. The photosensor system 300 is composed of a least two and preferably at least three photodetector units, with each photodetector unit spaced at least 25 m to 150 m, apart depending on the temporal resolution (time spacing between detected peaks) desired for velocity measurements, and a signal converter 340 such as a current preamplifier or resistor. Each of the plurality of photodetectors may be placed 0 to 180 degrees along the tracer's flight path. The photodetectors may be position so its field of view may capture any potential deviations in the tracer's flight or positioned to capture the maximum amount of light emitted from the tracer.

Each photodetector unit 310 is composed of a light detector 320, a lens 330 and optionally a filter 350. Considerations for selecting light detectors should take into account its sensitivity to detect light in the desired spectrum and its ability to detect low levels of light. Additionally, the detector's field of view must be adaquate to capture the tracer's light output so potential deviations in the tracer's flight path are still detectable. Examples of photodetectors units useful for detecting tracers emitting visible light include unamplified large area silicon detectors (Thorlabs, model SM1PD1A) and large area amplified silicon photodetectors (Thorlabs, model PDA 100) covering wavelengths of between 300 nm to 1000 nm. While lenses are recommended to gather and focus the light striking the light detector, it is also contemplated that light detectors can be used without the assistance of a lens if it has the sensitivity to efficiently capture the emitted light from a tracer. Examples of lens that may be utilized with silicon photodetectors include aspheric condensor lens (coated and uncoated), ranging in sizes from 25 mm diameter to 75 mm (Thorlabs ACL series). Another lensed detector is the International Light silicon detector coupled to a high gain L30 lens. These lens may be made of plastic or glass material depending on the desired optical properties. It is contemplated that the tracer characterization system disclosed herein may be used in daylight and nighttime conditions for measuring tracer light output. For daylight measurements, filters may be added to the photodetectors to reduce the level of ambient light striking the active area of the light detector. Exemplary filters include narrow band pass filters as well as high pass and low pass filters to control the ambient light from saturating the light detectors. Placement of the filters may be before or after the lens. The photosensor system may also include a signal converter 340 such as an current preamplifier or resistor, which converts current generated by the light detector into voltage signals for transmission. Exemplary signal converters include the Stanford model 570 low noise current preamplifier.

Figure 2B:
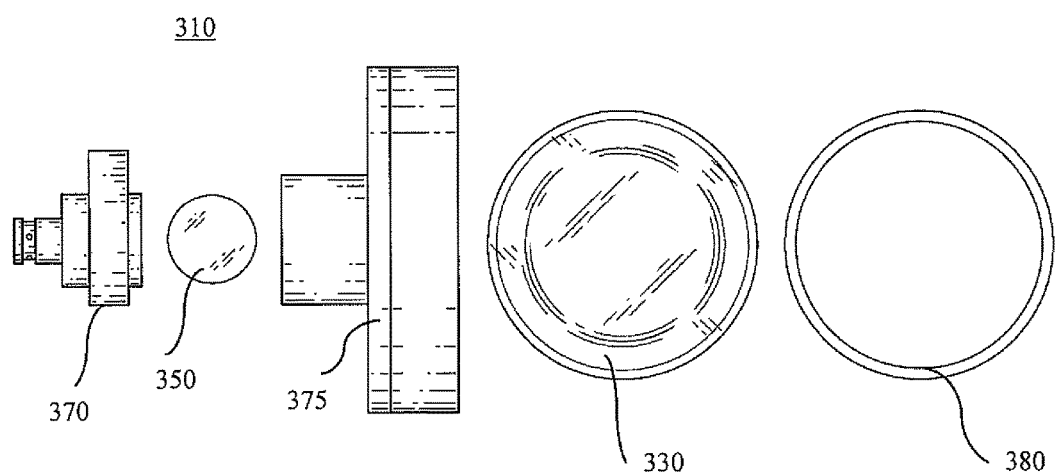
FIG. 2B is an exploded view of the units comprising the exemplary silicon photodetector unit of FIG. 2A.

In an exemplary photodetector unit 310 illustrated in FIG. 2A and FIG. 2B, a silicon light detector 320 is coupled to a 50 mm diameter glass aspheric condenser lens 330 and positioned inside a lens housing 375 with a retaining ring 380. The focal length of the lens is 40 mm, however, the lens to detector distance may be adjusted to minimize the diameter of the focused spot on the detector thereby maximizing the amount of light hitting the active area of the light detector. A filter 350 may placed in front of the light detector which is located inside the photodetector housing 370.

Light Signal Transmitter System

Figure 4:
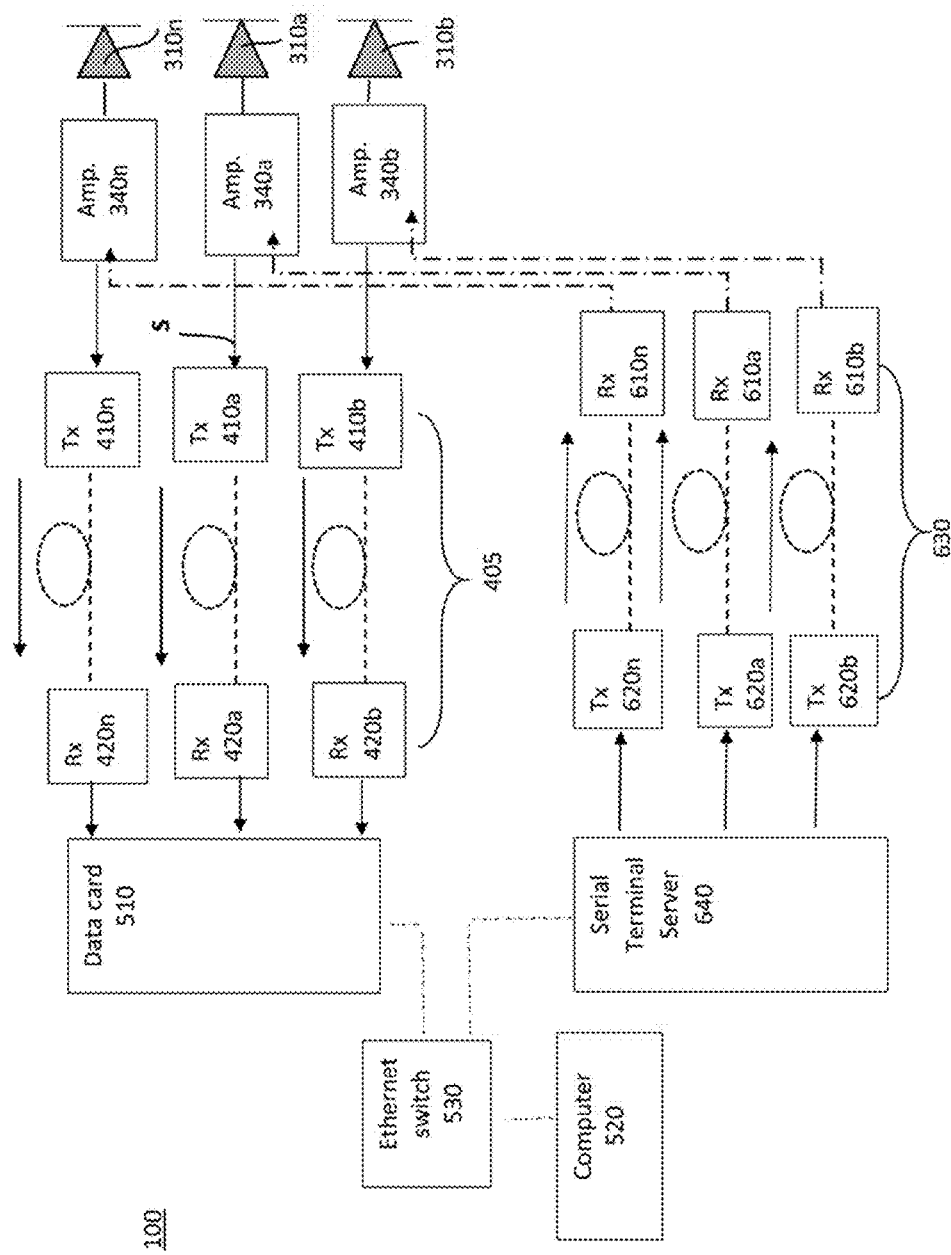
FIG. 4 is a schematic of an embodiment of the tracer light characterization system operated by a remote control system.

In FIG. 4, the light signal transmitter system 400 is comprised of a plurality of digital/analog (A/D) voltage converters units 405 that relays the light signal generated by its corresponding photodetectors units 310 over long distances to the data card 510. Each unit of the light transmitter system 400 may be composed of an A/D transmitter 410$n$ and an A/D receiver 420$n$ pair, that is directly coupled in series to a corresponding photodetector unit 310$n$. As illustrated in FIG. 4, a photodetector unit 310$a$ is connected to its corresponding A/D transmitter 410$a$ by a standard cable, S. The A/D transmitter 410$a$ coverts the analog signal into digital signal and sends the signal through a single or multimodal fiber optic cable 430 to its corresponding A/D receiver 420a. Exemplary digital/analog voltage converter units include the Model LTX5510 14-bit analog/digital (A/D) converter from Terahertz Technologies. The light transmitter system 400 can also transmit signals generated by the photodetectors at distances up to 10 km when single mode fiber optic cables are used. For short distance transmissions, standard connecting cables such as 50 ohm RG58 cables, without the need for digital/analog voltage convertors may be utilized. In another embodiment, the light signal transmitter system may be composed of a mix of standard cables and digital/analog voltage converter units connected by fiber optic cables depending on the transmission distance required. Additionally, the standard and fiber optic cables 430 described herein may be substituted by wireless systems.

Data Collection and Processing System

The data collection and processing system 500 is composed of a data card unit 510 that receives analog signals from the light signal transmitter system 400 and coverts such signals into digital signals, and a data processor unit (e.g. computer) 520. Exemplary data cards useful in the present invention include 16-bit simultaneously sampling data card available from National Instruments, (i.e. model 9215). A single data card may be utilized, however, it may be scaled to increase the number of inputs and output feeds from an increase in the number of transmitters. Data processor unit 520 such as a computer loaded with data collection and processing software, processes the data and displays it in a human readable format such as a chart, table or graph.

FIG. 3 is an exemplary schematic of the tracer light characterization system during operation. When a tracer bullet is fired from a gun, an acoustic trigger 200 is activated sending signals to the data card 510 to initiate data collection. The tracer bullet travels along a flight path which is perpendicular (90 degrees) to the field of view of at least the photodetector units 310 placed along the tracer's flight path. Each photodetector unit 310n is connected to an A/D transmitter 410n which in turn is connected to an A/D receiver 420n by a fiber optic cable 430n. When the fiber optic receiver 420n receives a digital signal generated by the transmitter 410n, it reconverts the signal to its original analog electrical signal. The data card 510 digitizes the analog signal which is transmitted for processing by a data processor 520. In FIG. 3, the distance between photodetectors, d, can be any distance deemed necessary for measuring the tracer's light intensity and velocity. Typical fiber distance distances can range from 25 m to 10 km as defined by the length of the fiber optic cable needed for the furthest detector. The transmitter/receiver design will ultimately determine the length of fiber that can be used between the receiver and transmitter.

Remote Control System

It is contemplated that at least one signal converter 340 and photodetector unit 310 can be controlled by an operator from a distant location by a remote control transmitter system 600. FIG. 4 illustrates an exemplary remote control system comprising an Ethernet serial terminal server 640 (such as Black Box LES6044A) and at least one RS232-fiber converter pair 630 (such as Black Box ME662A-SST). The Ethernet serial terminal server 640 combines multiple pairs of Ethernet-to-RS232 fiber converter 630 onto a single Ethernet cable that can be routed to the Ethernet switch 530. A pair of RS232 fiber converter is comprised of a RS232 fiber converter receiver 610 and an RS232 fiber converter transmitter 620 that are connected to each other by single or multi-modal fiber optic cable which can extend the range of transmission over longer distances compared to standard cables. The remote control transmission system 600 may be similarly configured as the light data transmission system 400, but instead relays digital instructions generated by the processor 520 to control the photosensor system 300. Thus commands can be sent from the computer to adjust the preamplifier settings by relaying the signals through the Ethernet switch, terminal server and a pair of RS232 fiber converters 650 to the corresponding preamplifier 340 connected to the photodetector unit 310. An indicator on the datacard may provide confirmation of the command. Alternatively, it is contemplated that data commands may be confirmed by an indicator signal generated by the photodetector or signal converter units. As with the light signal transmission system, the RS232 fiber converters in the remote control transmitter system may be substituted with a wireless system.

Example 1: Light Output Characterization

Silicon photodetectors were placed at positions A (closest to the gun barrel), B (mid distance from gun barrel), and C (farthest distance from gun barrel). Each photodetector was placed at a distance of at least 25 m from each other. Table 1 sets forth the photodetector and cable connection configuration at each location.

TABLE 1

| Position | Photodetector | Lens | Cable Connections between the A/D Receiver and A/D Transmitter |
|---|---|---|---|
| A | silicon PDA100 | glass aspheric lens | Copper coaxial (RG58U) |
| B | International Light L30 photometrically calibrated photodetector | lens configured by International Light | Copper coaxial (RG58U) |
| C | silicon PDA100 | glass aspheric lens | A/D fiber optic (Terahertz Technologies, Inc., LTX5510) |

Figure 5:
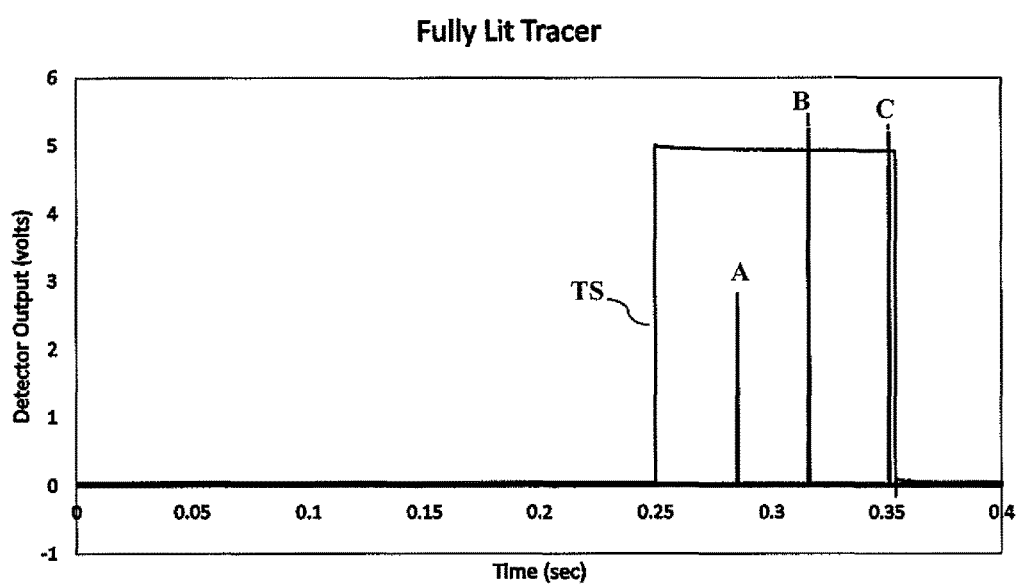
FIG. 5 is a graph measuring strong light output signals generated by a fully lit tracer as it passes detectors placed at position A, B, and C.

When the gun is fired, the acoustic trigger produces an electrical pulse (square wave) that triggers the data collection system to start collecting data. As a tracer round, such as the M62 tracer round, passes by each photodetector, the photons emitted from the tracer is collected by the lens and focused onto the surface of the photodetector. An example of the measurements captured by the data collection and processing system of a fully lit tracer is given in FIG. 5 for photodetectors placed at positions A, B and C. For the tested tracer, the light signature was very strong, almost saturating all three detectors as indicated by the voltage peaks at positions A, B and C. The tracer pulse signal (TS) illustrated in FIG. 5 indicates the system is activated for data collection at all three positions.

Figure 6:
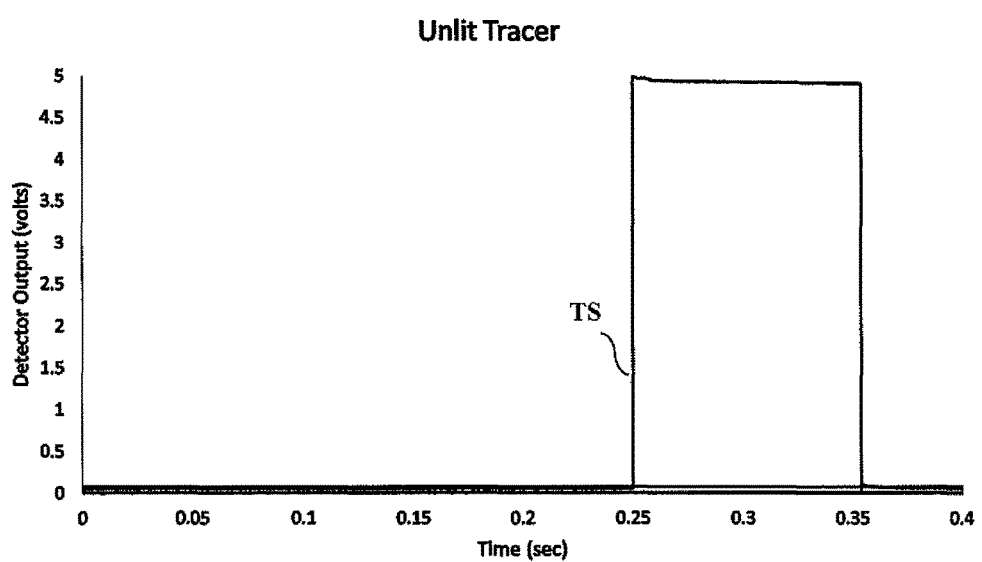
FIG. 6 is a graph showing no light output signals from a tracer that is unlit as it passes detectors placed at positions A, B, and C.

FIG. 6 shows the resultant signals from a "blind" tracer at positions A, B and C (without pyrotechnic material). In this case when the gun was fired, an acoustic signal (square wave) was produced by the acoustic trigger but no light was produced by the tracer so there is no light signal (i.e. no voltage) in either of the three detectors positioned at A, B and C.

Figure 7:
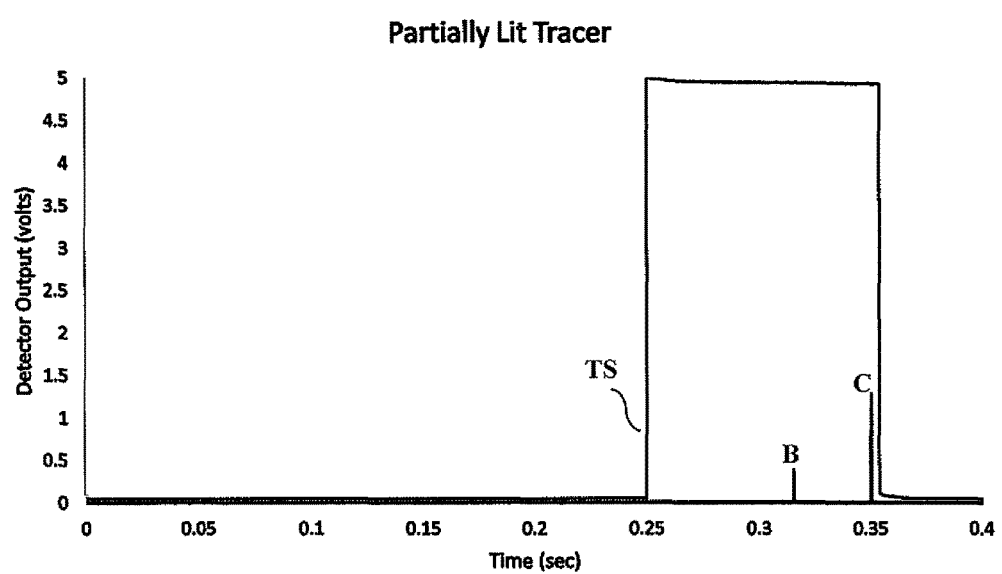
FIG. 7 is a graph showing a moderate signal output from tracer that is partially lit as it passes detectors placed at positions A, B, and C.

In FIG. 7, a partially lit tracer was fired. The tracer was not emitting any light at detector A, but only partially emitting light for the last two detectors, B and C. This is evident from the low voltage recorded by each of the detectors at positions B and C.

The voltage level of each channel is indicative of the strength of the light signal striking the detector. The stronger the light signal, the higher the voltage level. While the experiments disclosed herein reported the output in voltage, it is possible to convert output voltage to light intensity by calibrating the voltage output of the detector against a light source with a known optical output such as a calibrated lamp (i.e. tungsten halogen) or an integrating sphere. For instance, the L30 detector located at position B was calibrated by International Light against a calibrated lamp.

Example 2: Velocity Characterization

The tracer characterization system described herein can simultaneously measure both the light intensity and velocity of a fired tracer. Tracer velocity can be calculated using the light output characterization data. It is preferred to have a high data collection rate for accurate velocity calculations. In one embodiment, data was collected at 50,000 samples per second (or 20 μs spacing between adjacent data points). With more than two photodetectors, an average tracer velocity can be calculated from each (velocity of the tracer between two photodetectors) by the following equation:

$$V = \frac{\Delta x}{\Delta t}$$

Where V is the average velocity (between two detectors), $\Delta x$ is the distance between detectors, and $\Delta t$ is the time difference between signal maximum for each detector. For example, in FIG. 5 the average velocity between the first (Position A) and third detector (Positioned C) is calculated by using the time at maximum recorded light signal and the distance between the two detectors:

$$V = \frac{85 \text{ m} - 30 \text{ m}}{350.6 \text{ ms} - 285.3 \text{ ms}}$$

$$V = 765.7 \frac{\text{m}}{\text{s}} \left(2512.1 \frac{\text{ft}}{\text{s}}\right)$$

Using multiple detectors, it is possible to map the decrease in velocity as the tracer moves downrange by calculating the velocity between adjacent pairs of photodetectors.

The system described here can be easily scaled by increasing the number of photodetectors, its corresponding A/D voltage converter units, and data collection and processing capacity.

The embodiments set forth above are for illustrative purposes only and it is recognized that numerous variations may be made with respect to the system's units and sub-components. Therefore, while the invention has been disclosed in various forms only, it will be obvious to those skilled in the art that additions, deletions and modifications can be made without departing from the spirit and scope of this invention, and no undue limits should be imposed, except as to those set forth in the following claims.

What is claimed is:

1. A system for characterizing a tracer's light output during flight comprising:
    an acoustic trigger;
    a plurality of photodetector units situated along a travel path of a light emitting tracer for collecting light emitted by the tracer;
    a light signal transmitter system comprising at least one coupled A/D transmitter and A/D receiver pair, wherein the at least one coupled A/D transmitter and A/D receiver pair is coupled to a corresponding photodetector from the plurality of photodetector units; and
    a data collection and processing system comprising a data card and a data processor, and wherein the data card is connected to the acoustic trigger and the data processor.

2. The system of claim 1, further comprising a gun for firing a tracer that emits light.

3. The system of claim 2, wherein the tracer comprises a material located at the base of the tracer that emits visible light.

4. The system of claim 1, wherein the at least one A/D transmitter and A/D receiver pair is connected by a fiber optic cable.

5. The system of claim 1, wherein at least one photodetector comprises a light detector, a lens and a filter.

6. The system of claim 5, wherein the light detector is a silicon photodetector and the lens is an aspheric condenser lens.

7. The system of claim 1, wherein the photodetectors further comprises a preamplifier or resistor.

8. The system of claim 1, wherein the plurality of photodetectors are arranged at least 25 m apart from each other.

9. The system of claim 1, further comprising a remote control system.

10. The system of claim 9, wherein the remote control system comprises an Ethernet switch, a serial terminal server, and an RS232-fiber converter pair.

11. The system of claim 1 wherein the photodetectors are located at an angle of 0 to 180 degrees along the flight path of the tracer.

12. A method for measuring a tracer's light intensity and velocity during flight using the system of claim 1.

13. A method for characterizing a tracer's light output and velocity during flight comprising:
    a. firing a tracer comprising a material that emits visible light;
    b. collecting the tracer's emitted light using a plurality of photodetectors arranged 0 to 180 degrees along the flight path of the tracer, wherein at least one photodetector is connected to at least one coupled A/D receiver and A/D transmitter pair;
    c. transmitting the collected light signal from the at least one photodetector to the corresponding A/D receiver, wherein the corresponding A/D receiver converts the light signal from the photodetector into a digital signal;
    d. transmitting the digital signal to a corresponding A/D receiver wherein the at least one A/D receiver converts the corresponding digital signal to an analog signal and sending the analog signal to a data collecting system; and
    e. processing the signal transmitted by the data collecting system to generate a maximum recorded light signal.

14. The method of claim 13, further comprising calculating the velocity information of the fired tracer using the generated maximum recorded light signal.

15. The method of claim 13, wherein at least one of the plurality of the photodetectors comprises a light detector, a lens and a filter.

16. The method of claim 14, wherein the processed signal is displayed as light intensity and velocity data.

17. The method of claim 13, further comprising controlling at least one photodetector from a remote location using an Ethernet switch, serial terminal server and RS232-fiber converter pair.

18. The system of claim 1, wherein at least one photodetector comprises a narrow band filter.

* * * * *